US00PP14299P39

(12) United States Plant Patent
Teague

(10) Patent No.: US PP14,299 P3
(45) Date of Patent: Nov. 11, 2003

(54) APPLE TREE NAMED 'IRENE'

(50) Latin Name: *Malus pumila, Mill.*
Varietal Denomination: Irene

(76) Inventor: Glen A. Teague, 1055 Mendiola Rd., Nyssa, OR (US) 97913

( * ) Notice: Subject to any disclaimer, the term of this patent is extended or adjusted under 35 U.S.C. 154(b) by 5 days.

(21) Appl. No.: 10/075,139

(22) Filed: Feb. 13, 2002

(65) Prior Publication Data

US 2003/0154527 P1 Aug. 14, 2003

(51) Int. Cl.[7] ..... A01H 5/00

(52) U.S. Cl. ..... Plt./161

(58) Field of Search ..... Plt./168, 161

*Primary Examiner*—Anne Marie Grunberg
(74) *Attorney, Agent, or Firm*—Klarquist Sparkman, LLP

(57) ABSTRACT

A new and distinctive variety of an apple tree, named 'Irene,' distinguished by an early harvest date, large fruit, typical annual double-blooming when grown in Nyssa, Oreg., and field resistance to powdery mildew and fire blight.

3 Drawing Sheets

Latin name of the genus and species of the plant claimed: *Malus pumila,* Mill.
Variety denomination: 'Irene'.

BACKGROUND OF THE INVENTION

The present invention relates to a new and distinct variety of apple (*Malus pumila,* Mill.), which was discovered in Nyssa, Oreg., growing in a cultivated area in a block of BC 2 'Fuji' (not patented) apple trees. These trees were growing on 'M 26' rootstock (not patented) and had been planted Mar. 15, 1996. During the summer of 1996, I noticed a tree that was different in growth habit and leaf and fruit appearance from adjacent trees in the block. This tree was the result of budding from a bud stick taken from a limb sport or seedling mutation that was used to graft this tree of my new variety that I found. Subsequently, two additional identical trees were found in the same orchard. These trees had been grafted or budded from plant material from the same plant used to propagate the first tree of my new variety that I discovered.

BRIEF SUMMARY OF THE INVENTION

The first asexual propagation of my new variety was performed in August, 1997 in Nyssa, Oreg. by budding onto 'EMLA 26' (not patented rootstock). Subsequent asexual propagation of additional trees in Nyssa, Oreg. has been accomplished by grafting buds onto 'EMLA 9' (not patented) rootstock, onto 'Geneva 16' (unpatented) rootstock and onto 'M9' (not patented) rootstock. Incompatibility was subsequently observed in the trees budded onto 'Geneva 16' rootstock. Several trees of my new variety have been tested by the U.S.D.A. Research Station in Wenatchee, Wash. for fire blight resistance.

Asexual reproduction by budding in Nyssa, Oreg. as set forth above has shown that the characteristics of my new variety are established and are transmitted through succeeding asexual propagations.

Certain characteristics of this variety, such as growth and color, may change with changing environmental conditions (e.g., photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to the Munsell Book of Color, Kollmorgen Instruments Corp., 405 Little Britain Road, New Windsor, N.Y. 12553.

BRIEF DESCRIPTION OF THE PHOTOGRAPHS

The accompanying color photographs show typical tree, fruit, flower and leaf specimens of my new apple tree variety and depict the color as nearly true as is reasonably possible to make the same in a color illustration of this character. It should be noted that colors may vary with growing conditions and time of year as well as with lighting conditions at the time the photographs are taken.

DETAILED BOTANICAL DESCRIPTION

Figure 1:
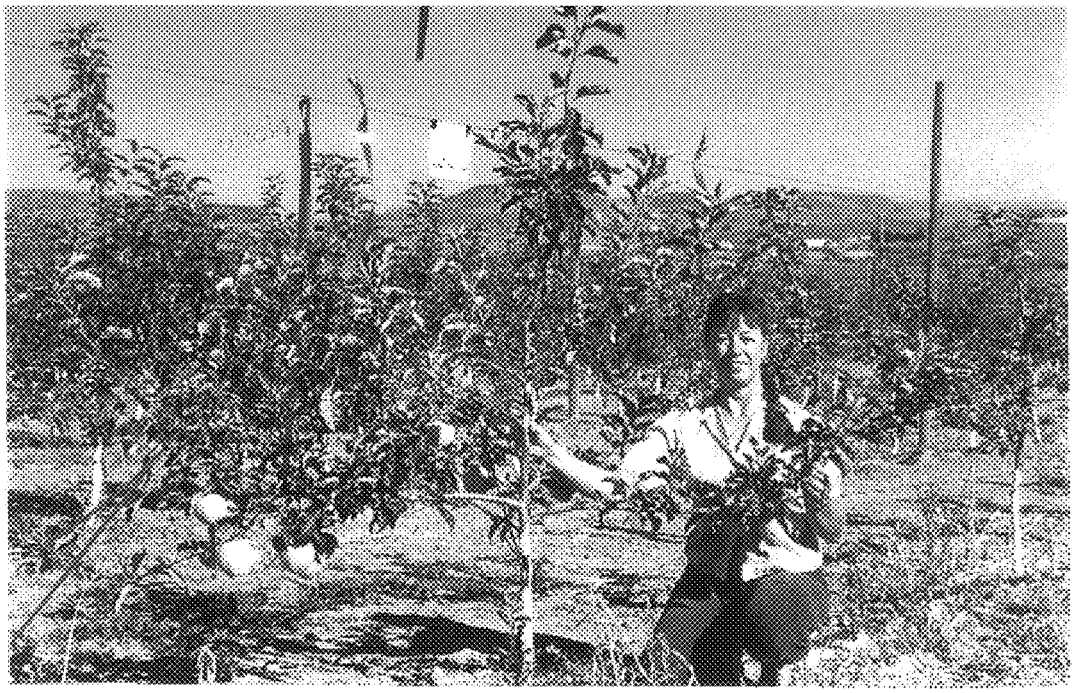
FIG. 1 is a photograph of a tree of the 'Irene' variety grafted onto 'M26' rootstock.
Figure 2:
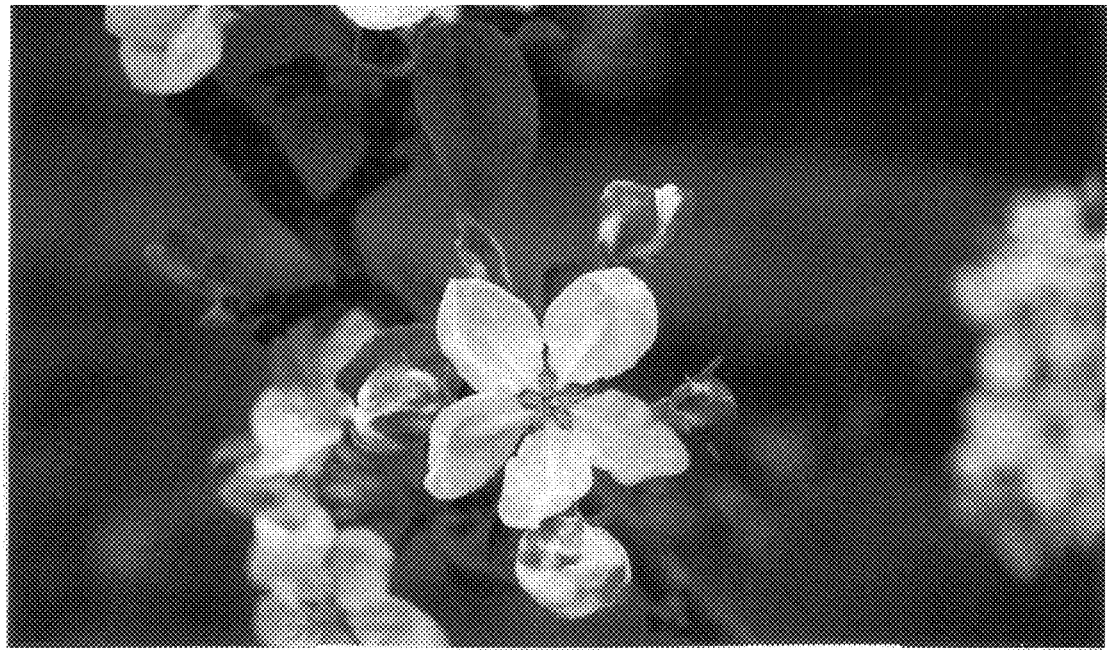
FIG. 2 is a photograph of a typical flower cluster from a tree of the 'Irene' cultivar.
Figure 3:
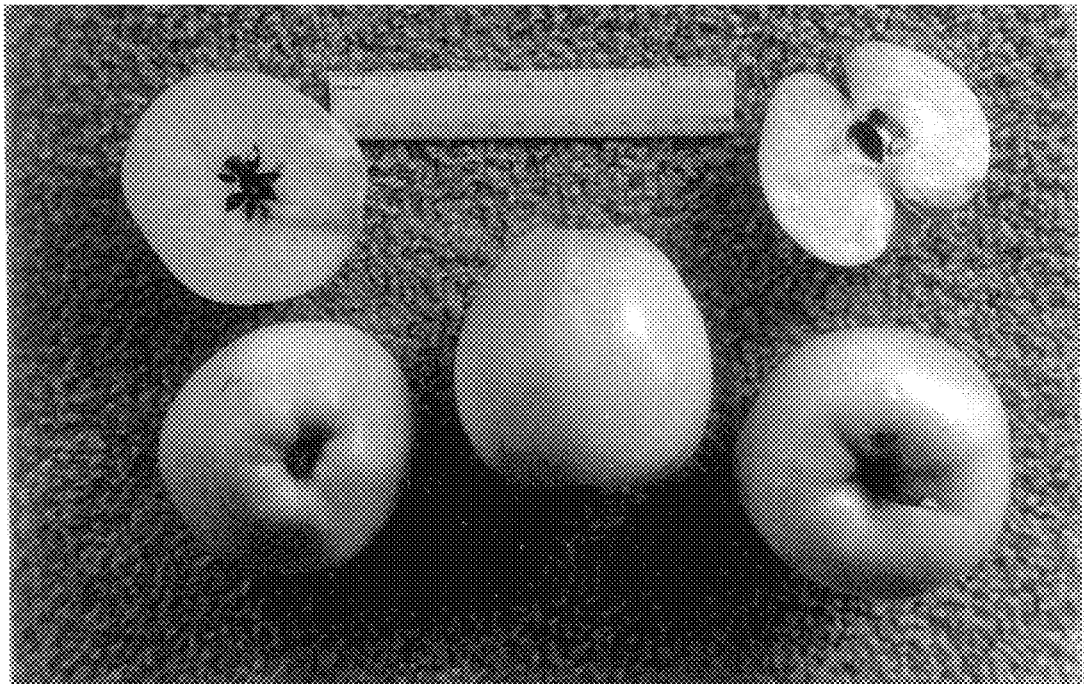
FIG. 3 is a photograph showing various aspects of typical 'Irene' fruit grown in Nyssa, Oreg. and showing cavity (stem end), basin (calyx end), side view, a transverse section and a longitudinal section.

The following detailed description of the 'Irene' cultivar apple tree is based on observations of the original trees of the variety from the 1996 planting and of two-year old, three-year old and four-year old progeny thereof growing in Nyssa, Oreg.

Scientific Name: *Malus pumila,* Mill. 'Irene'.
Parentage: Unknown parentage.
Tree:

*Vigor.*—High, average seasonal growth in Nyssa, Oreg., approximately 30 to 50 cm.

*Overall shape.*—Upright, spreading.

*Height.*—Height of original trees at about five and one-half years of age and growing on 'M 26' rootstock, about 4 m.

*Width.*—Overall spread of original trees at about five and one-half years of age about 3 m.

*Productivity.*—Highly productive, annual bearing, bears on one-year wood. Very precocious.

Trunk:

*Size.*—Original trees, caliper average 62 cm diameter at 0.5 m from ground line at about five and one-half years old.

*Trunk bark texture.*—Original trees, smooth, similar to that of standard 'Gala' trees (not patented).

*Trunk bark color.*—Original trees, grey-orange, 5 YR 4/4; distinctly lighter-colored bark than that of 'Ginger Gold', 7.5 YR 3/2.

Branches:

*Primary branches.*—Distinctly spreading, fairly limber, easily trained to wire. Two-year-old branches averaged 11 mm in diameter and 114 cm in length. Branch angle at emergence typically is 60 to 90 degrees from the vertical, wider than that of 'Ginger Gold' (typically 30 to 60 degrees).

*Branch color.*—One-year dominant shoot bark color grey-orange (7.5 YR 3/6), compared with 'Ginger Gold' at 7.5 YR 2/4 (brown); two-year-old branch at 5 YR 4/4 (light brown), color becoming lighter as wood ages.

*Branch pubescence.*—Glabrous to very finely pubescent, grey-green (5 Y 6/2).

*Branch lenticels.*—Elongated, 0.5×1 mm; light tan, (7.5 YR 6/2).

*Internodes.*—Average internode length on one-year-shoot 3.5 cm.

Leaves (observations were of ten leaves in June of 2001):

*Texture.*—Smooth with slight rugose on surface, typical of apple trees.

*Sheen.*—Somewhat glossy.

*Length.*—About 5.5 cm to about 7.0 cm, averaging about 6.0 cm.

*Width.*—About 3.0 cm to about 4.6 cm, averaging about 3.7 cm.

*Petiole.*—Medium. About 22 mm long and 2 mm in diameter. Color of petiole is dark purple (7.5 R 2/8).

*Form.*—Oval, tapering to tip.

*Margin.*—Finely serrate to crenate.

*Tip.*—Acute.

*Stipules.*—Present only on leaves of vigorous one-year shoots; variable in length from 6 to 15 mm, in width from 1 to 2 mm.

*Leaf color.*—Upwardly disposed surface: 5 GY 3/4 (dark green). Downwardly disposed surface: 5 GY 5/4 (medium green). Vein: 7.5 R 2/8 (reddish purple).

*Pubescence.*—Very fine, colorless.

Flowers (observations are from a sampling of typical flowers from a tree growing in Nyssa, Oreg.):

*Size.*—Individual flowers are medium size (typically about 40 mm fully open), similar in appearance to those of 'Ginger Gold,' but flowers of my new variety have a shorter pedicel (average length about 25 mm) when compared to 'Ginger Gold'.

*Bloom description.*—Flowers generally in clusters of five flowers per spur.

*Color.*—Bud (popcorn stage): bright pinkish purple (2.5 R 4/12). Fully open flower: upper side pure white, reverse side with remnants of pink color (2.5 R 6/6), fading to white as flower ages.

*Petals.*—Oblong, typical petals about 12 mm in length and about 10 mm in width.

*Stamen.*—Arranged in a single row. About 20 stamens, each about 6 mm in length.

*Filament.*—About 6 to 8 mm in length.

*Anthers.*—Light yellow (5 Y 8.5/10).

*Pistil.*—Stigma: Curving at distal end, round topped. Styles: Five, fused at base, approximately 8 mm in length.

*Sepals.*—Recurved downward, light green (2.5 GY 7/6), with fine, colorless pubescence. Sepals are about 7 mm in length, about 4 mm wide at base, recurved to expose persistent stamen.

*Pollen.*—Light yellow (5Y 8.5/10).Fragrance: Light, typical of other apple varieties.

*Time of bloom.*—2001, at Nyssa, Oreg.: First bloom April 17. Full bloom April 25. Petal fall May 5. This is considered early blooming, and it corresponded with the bloom period of Manchurian crabapple (not patented), but extending over a longer period. In Nyssa, Oreg., trees typically exhibit double-blooming in that a second lighter bloom occurs in late summer. However, fruit resulting from the second bloom has not matured before the arrival of winter. 'Ginger Gold' trees have rarely been observed to double bloom.

*Fertility.*—Diploid, long bloom period. Used successfully as pollinator for 'Gala' apple trees. Through 'Irene' may set fruit occasionally with its own pollen, it generally is considered to be self-sterile.

*Eye* (*calyx or calyx tube*).—Closed.

Fruit (observations from ten samples of typical fruit grown in Nyssa, Oreg., in August of 2001.)

*Shape.*—Round conic, usually symmetric; often ribbed and commonly with a lumpy crown (stem end). Length/diameter ratio approximately 1.06 (average of 10 fruit samples). Apex (calyx end) irregular, with distinct lobes varying in size and number.

*Size.*—Large to very large, sometimes exceeding 500 grams in weight. Consistently larger than 'Ginger Gold'. Average width about 7.0 to about 8.5 cm; average length about 7.5 to about 9 cm.

*Stem cavity.*—Broad, medium depth, about 43 mm wide by about 19 mm deep (average of 10 apples); obtuse to acute.

*Basin cavity.*—Medium breadth, about 35 mm wide and about 15 mm deep; deeper than that of 'Golden Delicious' (not patented) or 'Ginger Gold', with more prominent lobes.

*Stem.*—Medium to stout, about 15 to about 30 mm in length×about 2 mm in width, usually reaching to the crown of the fruit and sometimes beyond; greenish (10 Y 6/6), with colorless pubescence. Stem consistently shorter than that of 'Ginger Gold'.

*Locules* (*carpels*).—Medium size, five in number, usually open.

*Skin.*—Very thin, tender, very slow to become oily in storage; susceptible to russet, especially in the stem bowl (approximately 50%), in contrast to 'Ginger Gold', which claims to be free of this condition. My new 'Irene' cultivar has been observed to date to be free from stem bowl cracking, a common malady of apples as they reach advanced maturity.

*Lenticels.*—Generally sparse and inconspicuous (about 2 to 3 per square cm), with variable color from almost colorless to green (2.5 Y 6/10) or occasionally brownish (2.5Y 5/8). They generally are round in shape and vary in size from about 0.5 to about 1.0 mm.

*General color effect.*—Greenish yellow overall color (see below), quite variable, often with part of the fruit greenish and the remainder yellow to almost orange. General color effect similar to that of 'Ginger Gold'. Ground color: Greenish (2.5 Y 6/10). Over color: Yellow (5 Y 8/14), sometimes almost orange (7.5 YR 7/4) on surface exposed to sun. Russet: Often present flaring out from stem bowl; rarely on the side of the fruit. In comparison, russet is infrequently found in the stem bowl of 'Ginger Gold' apples. Flesh: Color cream (7.5 Y 9/4).

*Fruit characteristics at maturity when harvested (based on fruit tested early to mid-season, Aug. 6, 2001).*—Acid content: Low for early ripening variety, about 0.5% malic acid. Firmness: 19 to 23 pounds. Soluble solids: About 12 to 13%. Starch index: On a scale of 1 (high starch) to 6 (low starch), range about 2.0 to 2.5. Flavor: Sweet-tart. Juiciness: Very juicy. Aroma: Low. Samples were stored until Nov. 10, 2001 in common storage (2 to 4° C.), where they remained in good condition. Fruit analysis on November 10 was 11.5 pounds firmness, 12.6% soluble solids, and about 0.33% malic acid.

*Core.*—Mostly closed; occasionally open. Width: About 25 mm. Length: About 30 mm. Calyx tube: short, closed. Core lines: Weakly defined.

*Seed.*—Obovate in shape, 1 to 2 per cell; brown (5 YR 2/3), about 7 to 10 mm in length by about 4 to 5 mm wide.

*Fruit production.*—First picking date in 2001 was about August 6, and last picking date was about Aug. 9, 2001.

*Keeping quality.*—Very good for an early variety; fruit remains firm and crisp at room temperature for a week.

*Storage.*—Up to 5 months in common storage (0° C.); no data for controlled atmosphere (CA) storage, since this variety would be marketed immediately after harvest, before late-season varieties such as 'Golden Delicious' would be available.

*Usage.*—Primarily for fresh eating (dessert) within 2 to 3 months of harvest. Also excellent for culinary use because of its well-balanced sugar/acid ratio.

Hardiness: Unknown, been growing in Nyssa, Oreg.; Zone 3 on the USDA Climate Zone Chart.

Disease and insect resistance: Field observations over four years have shown that 'Irene' has high field resistance to fire blight (*Erwinia amylovora*) and powdery mildew (*Podosphaera leuchotricha*), while 'Ginger Gold' is extremely susceptible.

TABLE 1

Comparison of 'Irene' and 'Ginger Gold' Cultivars

| Characteristic | Irene | Ginger Gold |
|---|---|---|
| Average bloom date | April 20 | April 30 |
| Average harvest date | August 6 | August 16 |
| Double blooming | Almost annually produces a few late blooms | Rarely |
| Crop load | Heavy | Moderate |
| Average fruit stem length | 25 mm | 35 mm |
| Bark color | Tan (5 YR 4/4) | Brown (7.5 YR 3/2) |
| Branch angle | 60 to 90 degrees | 30 to 60 degrees |
| Russet in stem bowl | Common | Infrequent |
| Susceptibility to mildew and fire blight | Field tolerant | Highly susceptible |

Therefore, as shown in Table 1, 'Irene' is not the same variety as 'Ginger Gold.' In addition, 'Irene' is distinguishable from BC 2 'Fuji' because 'Irene' apples are generally yellow, while BC 2 'Fuji' apples are generally red. Furthermore, the apples of BC 2 'Fuji' mature at least 60 days later than the apples of 'Irene.' 'Irene' is distinguishable from 'M 26' dwarfing rootstock, because the apples of 'M 26' are small, greenish-yellow, soft and almost inedible.

I claim:

1. A new and distinct variety of apple tree named 'Irene', substantially as herein shown and described.

* * * * *